United States Patent
Sanders et al.

(10) Patent No.: US 10,343,267 B2
(45) Date of Patent: Jul. 9, 2019

(54) TOOL DEVICES FOR SECURING CONNECTOR ELEMENTS

(71) Applicant: MID CORP., West Orange, NJ (US)

(72) Inventors: Daniel Sanders, Ra'anana (IL); Ben Zion Spector, Tel Mond (IL)

(73) Assignee: MID CORP., West Orange, NJ (US)

( * ) Notice: Subject to any disclaimer, the term of this patent is extended or adjusted under 35 U.S.C. 154(b) by 209 days.

(21) Appl. No.: 14/786,592

(22) PCT Filed: Apr. 24, 2014

(86) PCT No.: PCT/IB2014/060993
§ 371 (c)(1),
(2) Date: Oct. 23, 2015

(87) PCT Pub. No.: WO2014/174486
PCT Pub. Date: Oct. 30, 2014

(65) Prior Publication Data
US 2016/0082577 A1 Mar. 24, 2016

(30) Foreign Application Priority Data

Apr. 25, 2013 (GB) .................................. 1307521.3
Dec. 31, 2013 (GB) .................................. 1323173.3

(51) Int. Cl.
B25B 15/00 (2006.01)
B25B 23/10 (2006.01)
(Continued)

(52) U.S. Cl.
CPC ........ *B25B 23/108* (2013.01); *A61B 17/8875* (2013.01); *A61B 17/8888* (2013.01);
(Continued)

(58) Field of Classification Search
CPC ... B25B 23/108; B25B 15/001; B25B 15/008; B25B 27/143; A61B 17/8875; A61B 17/8888
See application file for complete search history.

(56) References Cited

U.S. PATENT DOCUMENTS 3,288,184 A * 11/1966 Smith ................... B25B 15/005
81/443
3,695,321 A 10/1972 Garehime, Jr.
(Continued)

FOREIGN PATENT DOCUMENTS

| CA | 678265 A | 1/1964 |
|----|----------|--------|
| GB | 2495429 A | 4/2013 |

(Continued)

OTHER PUBLICATIONS

Search Report for International Patent Application PCT/IB2014/060993, dated Sep. 19, 2014.
(Continued)

*Primary Examiner* — Robert J Scruggs
(74) *Attorney, Agent, or Firm* — The Dobrusin Law Firm, P.C.

(57) ABSTRACT

A driver tool apparatus is provided for the secure gripping, driving insertion, and release of a broad range of connector and/or fixation elements such as screws or bolts. These driver devices can be utilized for a broad range of applications in many fields. The driver tool, in some embodiments, may include a driver shaft; one or more driver elements protruding from the driver shaft and having a base region proximate the driver shaft and a distal region away from the driver shaft, wherein each driver element includes one or more pins suitable for inserting into a socket having one or more inside walls; and one or more securing features on each driver element.

20 Claims, 6 Drawing Sheets

(51) Int. Cl.
*A61B 17/88* (2006.01)
*B25B 27/14* (2006.01)

(52) U.S. Cl.
CPC .......... *B25B 15/001* (2013.01); *B25B 15/008* (2013.01); *B25B 27/143* (2013.01)

(56) References Cited

U.S. PATENT DOCUMENTS

| | | |
|---|---|---|
| 4,007,768 A | 2/1977 | Matsushima |
| 4,466,315 A | 8/1984 | Boschetto et al. |
| 2005/0120838 A1 | 6/2005 | Gottlieb et al. |
| 2008/0269768 A1 | 10/2008 | Schwager et al. |
| 2009/0202959 A1 | 8/2009 | Ajlouni et al. |
| 2011/0098715 A1* | 4/2011 | Laubert ................ A61B 17/861 606/104 |

FOREIGN PATENT DOCUMENTS

| | | |
|---|---|---|
| WO | 1990/008510 A | 8/1990 |
| WO | WO 90/08510 * | 8/1990 |
| WO | 2009/115617 A1 | 9/2009 |
| WO | 2010/093658 A2 | 8/2010 |

OTHER PUBLICATIONS

Search Report for GB Patent Application 1304950.7 dated Aug. 13, 2013.
IPRP and Written Opinion PCT/IB2014/060993, dated Sep. 19, 2014.
Examination Report from the Australian Patent Office for Application No. 2014258975 dated Jan. 4, 2018.
Office Action from the Eurasian Patent Office for Application No. 201591917 dated Oct. 31, 2017.

* cited by examiner

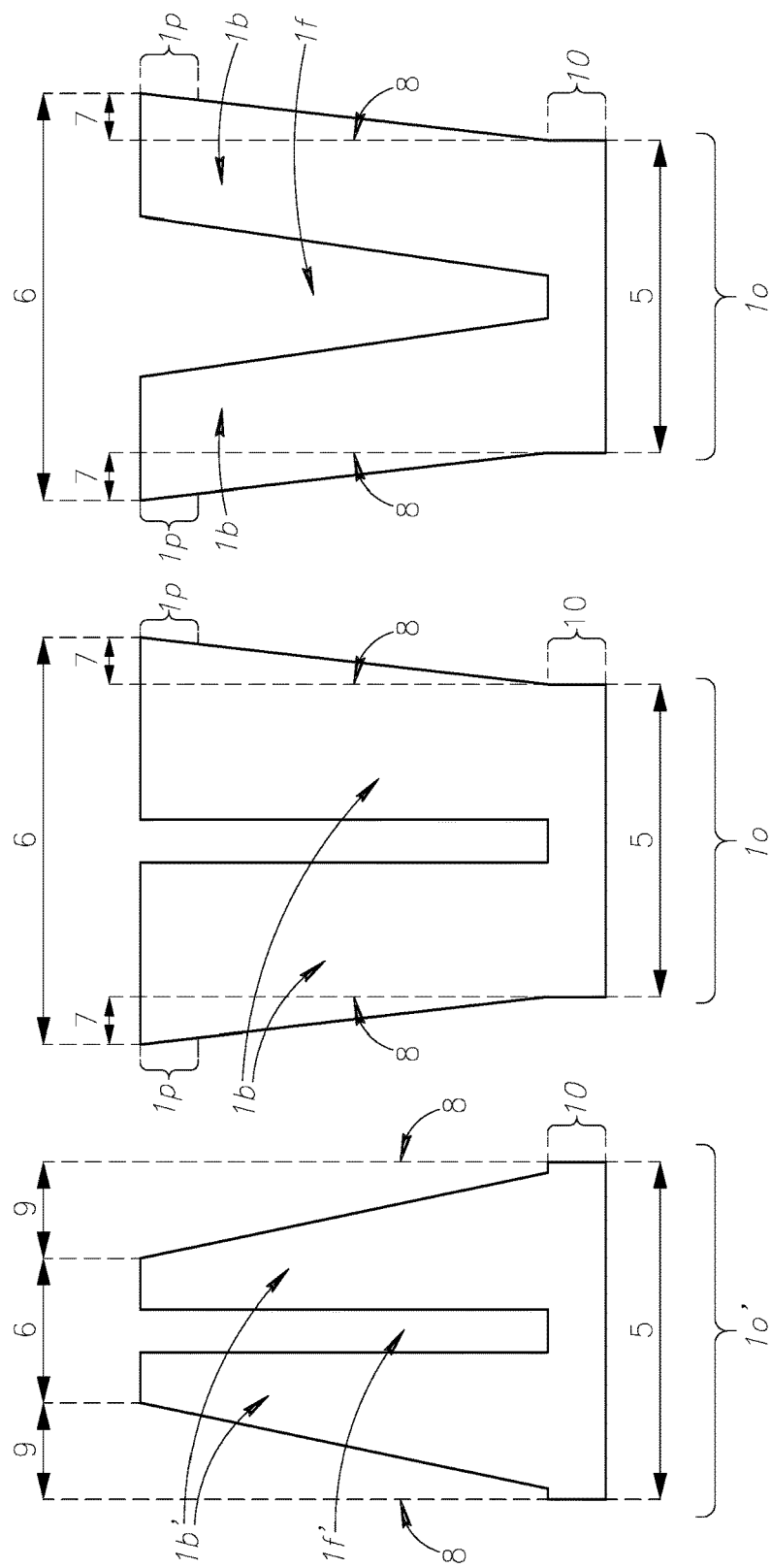

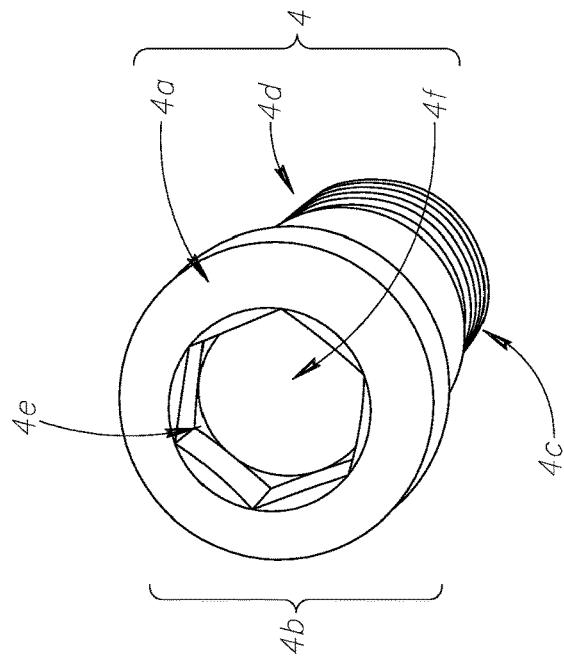
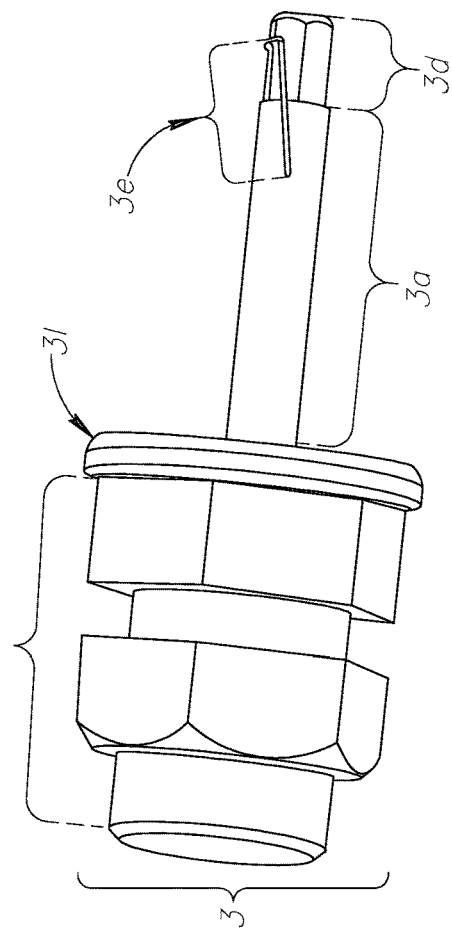
FIG. 2B
FIG. 2A

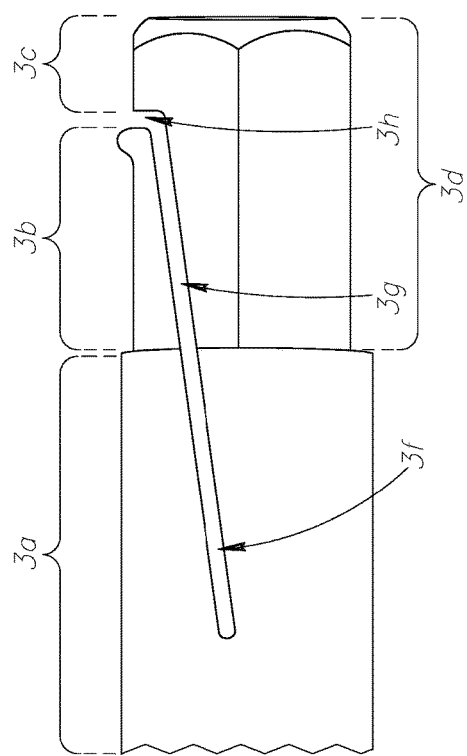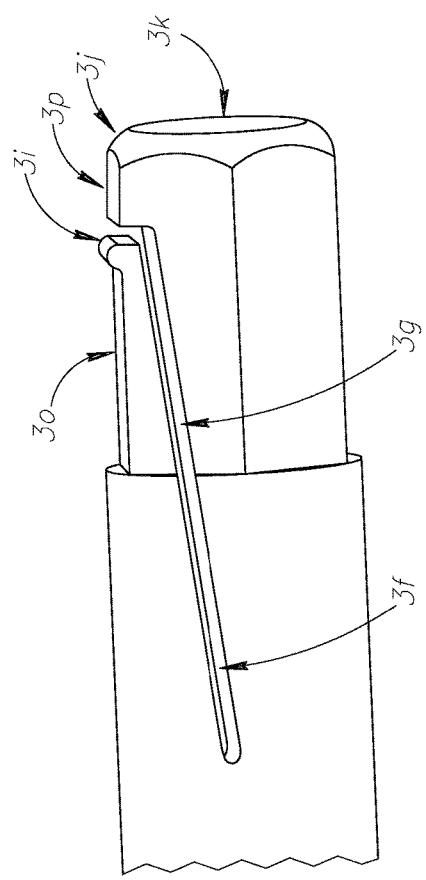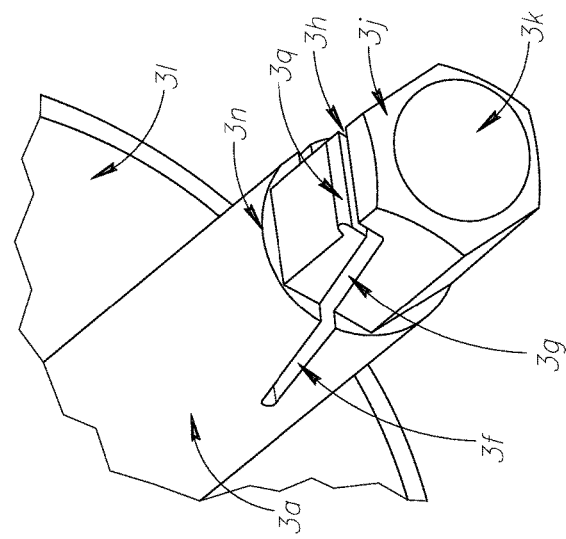

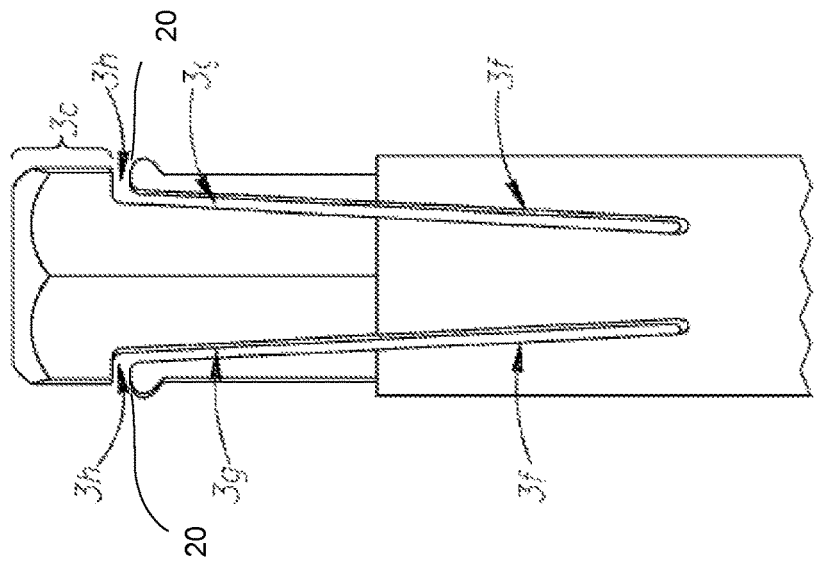
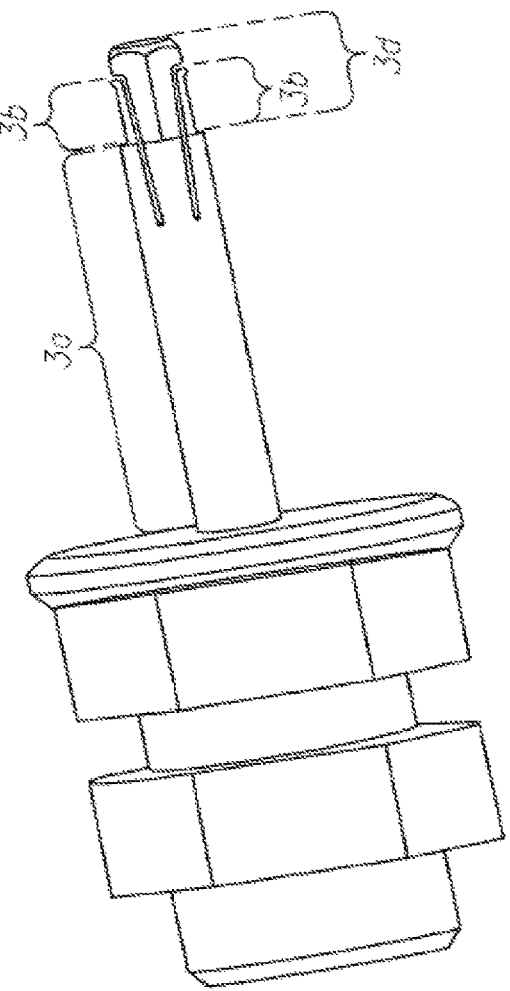

TOOL DEVICES FOR SECURING CONNECTOR ELEMENTS

FIELD OF THE INVENTION

The present invention relates generally to a driver tool apparatus, and more particularly to an improved means and method for the gripping, driving insertion and release of a broad range of connector and/or fixation elements.

BACKGROUND OF THE INVENTION

U.S. Pat. Appl. No. 2005/0120838 Gottlieb & Carroll discloses a driving tool with a driving element whose design comprises a single pair of two separate jaws with a rectangular outer peripheral cross-section separated by a gap or slit which extends to the tip of the driving element and that attempts to directly engage the socket in the head section of a fixation/screw element. This gap or slit between the two jaws of this prior art is cut in a parallel axis to each of the jaws. The two jaws are shaped so that the distal ends of each jaw taper in a convergent manner from the proximal ends of the jaws so that when they are inserted into the socket of the screw/bolt the two convergent jaws further converge (compress) towards each other creating a release angle between the two jaws and the socket. Therefore this prior art teaches a severely flawed design from an engineering perspective that in fact does not provide adequate gripping force (retention) of the jaws of its driving element in the socket of the screw/bolt.

As described above, the cited prior art's driving element of its driver tool is also specifically limited to two and only two jaws, and said single pair of jaws are limited to an outer rectangular cross-sectional shape for insertion into a polygonal socket.

As described above, the driving element of any improved driver tool is subjected to two stress forces when it is both: i. initially directly engaging (frictionally) the socket (in the head) of the screw/bolt. ii. driving (screwing) the screw/bolt into its target site.

Engineering analysis as described above of the driver design of the cited prior art reveals that: i. insertion of a single set of two separate jaws into multiple sockets of different screws/bolts and ii. the driving of said bolts/screws by this prior art design result in: loss of frictional engagement of this driver tool upon insertion into sockets of screws/bolts and permanent collapse of the single pair of jaws of the driving element of this driver tool when attempting to drive said screws/bolts into their target sites.

SUMMARY OF THE INVENTION

Reusable tool devices is provided for the secure gripping and driving of a broad range of connector and/or fixation elements such as screws or bolts. These tool devices can be produced in kits of various sizes and lengths and utilized for a broad range of applications in many fields.

In some embodiments, a driver tool is provided, that includes a driver shaft having an axis of rotation for driving a fixation component; one or more driver elements protruding from the driver shaft and having a base region proximate the driver shaft and a distal region away from the driver shaft, wherein each driver element includes one or more pins suitable for inserting into a socket having one or more inside walls; one or more securing features on each driver element, wherein the securing features of a driver element, individually or collectively, frictionally engage the one or more inside walls of the socket using a spring force; wherein each securing feature includes one or more flexing arm(s) that are attached to a pin or a portion of a pin, each flexing arm having a protrusion extending in an outward direction and/or having an outside wall that forms an obtuse angle relative to the normal of the axis of rotation and in the direction of the body of the flexing arm(s) and each securing feature includes one or more slits in the driver element extending generally in the distal direction for receiving a portion of the flexing arm; one or more guide features along each flexing arm for guiding the driver element into the socket and compressing the flexing arm towards one of the slits for providing the spring force; wherein the driver tool includes a plurality of driver elements or includes a driver element having a non-circular shape; and wherein the securing features are arranged so that the torque force required for driving a fixation component is generally decoupled from the frictional force for engaging the socket of the fixation component.

In a further embodiment, the driver tool is a multi-socket tool comprising two or more driver elements, each driver element is configured for fitting into a socket having a generally circular cross-section.

In further embodiments, each driver element has a center, a pin that is divided into a first and a second flexing arm by the slit interposed between the first and second flexing arms; wherein the first flexing arm is closer to the axis of rotation than the second flexing arm, the slit direction in the plane perpendicular to the axis of rotation is generally in the direction of rotation at the position of the driver element.

In further embodiments, the separation distance between the flexing arms in the region near the base of the driver element is less than the separation distance between the flexing arms in the distal region of the driver element.

In further embodiments, each flexing arm of the driver tool has a cross-section in the plane perpendicular to the axis of rotation that is generally a circle segment, where a circle segment is defined by the area of a circle that is cut off by a chord.

In further embodiments, the cross-section of the flexing arm changes at different distances from the driver shaft.

In further embodiments, the each flexing arm has generally the same shape.

In further embodiments, an axis in the base of the flexing arms is oriented in a distal direction that is generally parallel to the axis of rotation of the driver shaft.

In further embodiments, the rotational force acting on each driver element for driving a fixation component is generally perpendicular to the frictional force for securing the driver element to the fixation component.

In further embodiments, the driver tool includes a single driver element and the driver element has a non-circular shape for inserting into a socket of a fixation component having generally the same non-circular shape so that any rotational motion of the driver element about the axis of rotation of the driver shaft rotates the fixation component.

In further embodiments, the driver slit is angled relative to the axis of rotation.

In further embodiments, the flexing arm has a protrusion located near the distal region of the flexing arm and extending away from the center of the driver element.

In further embodiments, the slit extends into the driver shaft.

In further embodiments, the cross-section of driver element generally has the shape of a regular hexagon.

In further embodiments, the cross-section of the driver element is generally uniform, except for the guide feature and the slit.

In further embodiments, the driver element includes a vertical through slit section and a longitudinal through slit section for defining the flexing arm, wherein the flexing arm is a spring clip.

In further embodiments, multiple sets of vertical and longitudinal through slit sections are incorporated in the driver element for defining multiple flexing arms, wherein each of the multiple flexing arms is a spring clip.

In further embodiments, the guiding feature is a taper or curved region on the leading edge of the flexing arm, positioned so that the flexing arm is automatically compressed inward towards the slit when the driver element is inserted into a socket.

According to some embodiments, a process is provided, that includes: providing a driver tool and a fixation component having one or more sockets; engaging each of the one or more driver elements of the driver tool by inserting each driver element into one of the sockets of the fixation component; rotating the driver tool so that the fixation component is rotated and/or driven into a component to which it becomes attached; disengaging the driver tool from the fixation component; wherein the step of engaging includes a step of compressing a flexing arm towards a slit so that the driver element can fit into the socket, wherein the flexing arm creates a spring force against a wall of the socket.

In some embodiments, the step of rotating the driver tool creates a driving force on an internal wall of each of the sockets, wherein the driving force is perpendicular to the spring force.

In further embodiments, the flexing arm returns to an initial position upon disengaging the driver tool from the fixation component.

In further embodiments, the fixation component is a headless screw having a shaft and a bottom wall, wherein the bottom wall limits the depth of insertion of each driver element into a corresponding socket of the fixation component.

According to yet further embodiments, a driver tool is provided, that may include: a driver shaft having an axis of rotation for driving a fixation component; a driver element protruding from the driver shaft and having a base region proximate the driver shaft and a distal region away from the driver shaft, wherein the driver element includes a pin suitable for inserting into a socket having one or more inside walls; one or more securing features on each driver element, wherein the securing features of a driver element, individually or collectively, frictionally engage the one or more inside walls of the socket using a spring force; wherein each securing feature includes a spring clip mechanism forming a flexing arm(s) that is attached to the pin or a portion of the pin, the flexing arm having a protrusion extending in an outward direction and/or having an outside wall that forms an obtuse angle relative to the normal of the axis of rotation and in the direction of the body of the flexing arm(s) and each securing feature includes one or more slits in the driver element extending generally in the distal direction for receiving a portion of the flexing arm; and one or more guide features along said flexing arm for guiding the driver element into the socket and compressing the flexing arm towards a slit for providing the spring force.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein:

FIG. 1A is a schematic illustration of a side perspective of a negative tension prior art Socket driver pin element;

FIG. 1B is a schematic illustration of a side perspective of an exemplary Socket driver pin element, according to some embodiments;

FIG. 1C is a schematic illustration of a side perspective of an exemplary Socket driver pin element with an enhanced wedge, according to some embodiments;

FIG. 1Fb is a schematic illustration of the top side of a double socket bolt, according to some embodiments;

FIG. 2A is a schematic illustration of a side perspective of a Spring clip driver tool, according to some embodiments;

FIG. 2B is a schematic illustration of a top perspective of a bolt associated with a Spring clip driver tool, according to some embodiments;

FIG. 2C is a schematic illustration of a close up side view of a top section of a Spring clip driver tool, according to some embodiments;

FIG. 2D is a schematic illustration of a close up angled view of a top/side section of a Spring clip driver tool, according to some embodiments;

FIG. 2E is a schematic illustration of a close up top side angled view of a top section of a Spring clip driver tool, according to some embodiments;

FIG. 2F is a schematic illustration of a side view of a top section of a Spring clip driver tool with two spring mechanisms, according to some embodiments; and FIG. 2G is a schematic illustration of a close up side view of a top section of a Spring clip driver tool with two spring mechanisms, according to some embodiments.

Figure 1E:
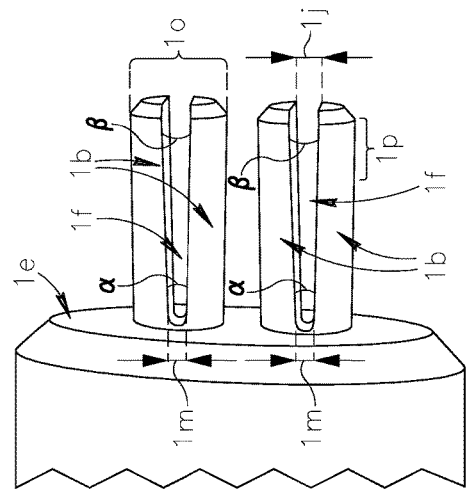
FIG. 1E is a schematic illustration of a close up side perspective of a top section of a Multi-socket driver tool with 2 driver pins, according to some embodiments.
Figure 1G:
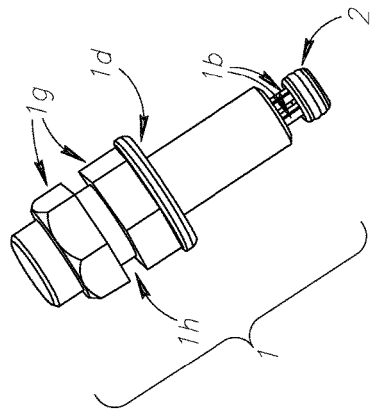
FIG. 1G is a schematic illustration of a side perspective of a Multi-socket driver tool with 2 driver pins coupled to a double socket bolt, according to some embodiments.

It will be appreciated that for simplicity and clarity of illustration, elements shown in the drawings have not necessarily been drawn to scale. For example, the dimensions of some of the elements may be exaggerated relative to other elements for clarity. Further, where considered appropriate, reference numerals may be repeated among the drawings to indicate corresponding or analogous elements throughout the serial views.

DETAILED DESCRIPTION OF THE INVENTION

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments.

The secure gripping of multiple fixation/connector elements by a reusable driver tool so that these same elements can be driven (screwed) into a target bore (threaded or unthreaded) or a completely unprepared target site and the driver tool can then be rapidly and easily disengaged from the fixation/connector element (screw/bolt) without changing in any way the position of the fixation/connector element in the target site into which it has been inserted by the driver tool is an engineering challenge.

It will be appreciated that a driver tool that is to enable improved functionality above the tools known in the art, must incorporate a driving element whose design allows for its insertion into a socket of the fixation/connector element located within the head portion or body of the fixation/connector element.

It will be further appreciated that an improved driving tool should incorporate in its design a driving element whose outer side walls should adapt and fit as snugly as is possible when inserted multiple times into different internal side walls of the sockets of the multiple fixation/connector elements so as to provide adequate and direct frictional engagement of the driver tool to the fixation/connector elements.

It will be further appreciated that the design of the driving element of the improved driver tool should be engineered to allow for multiple use of the tool (multiple driving) without loss of engagement (frictional fit) of the driving element in the socket of the fixation/connector element after repeated use of the driver tool to drive (screw) numerous different fixation/connector elements (screw/bolts). Additionally, the driving element should be designed to enable rapid and easy release from the screw or bolt being inserted or extracted, when required, with negligible effect on the screw or bolt position.

It will be appreciated that the driver element of the improved driver tool may be placed under stress forces when it is initially engaging (frictionally) by sliding into the socket of the screw/bolt, and when driving (screwing) the screw/bolt into its target site.

According to some embodiments of the present invention, a driver element whose design maintains direct engagement (frictional fit) for only a few insertions of the driver tool into a few sockets of several screws/bolts has limited value to the user as it will require the user to purchase many such tools when placing numerous fixation/connector elements (screws/bolts). A driver tool whose design fails to allow for maintaining this snug engagement when the driver tool is used to actively drive (screw) multiple screws/bolts will also be of limited value to the user.

Non-limiting embodiments of the invention include a one time or reusable improved driver tools which may include, in a first embodiment, a multi-socket driver tool, and in a second embodiment, a spring-clip socket driver tool, as described below.

Other embodiments of the invention may have grasping elements such as hand-held grasping features or elements which differ from those described below.

Reference is now made to FIGS. 1D-E and 1G-1J, which are graphical illustrations of different views of a Multi-socket driver tool and associated bolts, according to some embodiments, for enabling multiple use of the driver tool without loss of engagement of the driving element in the socket of fixation/connector elements, and rapid release from the screw or bolt being inserted or extracted, when required, with negligible effect on the screw or bolt position.

For example, Multi-socket driver tool 1, includes Head section 1a, Shaft body limiting flange 1d, Driver shaft body 1c, Socket driver element limiting flange 1e and Socket driver pin elements 1b Multi-socket driver tool 1 features two or more sets of (i.e. multiple) flexing arms 1b, whose outer peripheral cross-sectional shape is preferably substantially round with slits cut into each set of the driver pin elements 1o, and where each driver pin element 1o slides into a separate socket (whose cross-section preferably is correspondingly round) of a multiple socketed head of each fixation/connector element. As can be seen in one embodiment in FIG. 1C, Socket driver pin element slit if shows how each slit may be purposefully cut at a divergent angle to each half section of each pair of driver pins. Each multi-driver pin element 1o is purposely milled so that each flexing arm 1b diverges from the other. When these diverging engagement elements are inserted into its corresponding socket, each divergent angle slit allows for each set of flexing arms outer side walls to separately frictionally engage (via a spring action of each flexing arm of each pin) the internal side walls of each separate and corresponding socket of the multiple socketed head of each screw/bolt, without permanently collapsing each of the driver pin elements.

In general, pin elements 1o may be configured perpendicular to Socket driver element limiting flange 1e, however they may be angled as well. In general, slits if may be configured to be in parallel with one another. For example, as seen in FIG. 1D, each pin diverges in its angle from its proximal end, as can be seen in FIG. 1B, such that the resulting spring tensions when inserted into the socket of the screw/bolt cause the desired wedge effect. In still further embodiments slits if may be tapered as seen in FIG. 1C.

Figure 1D:
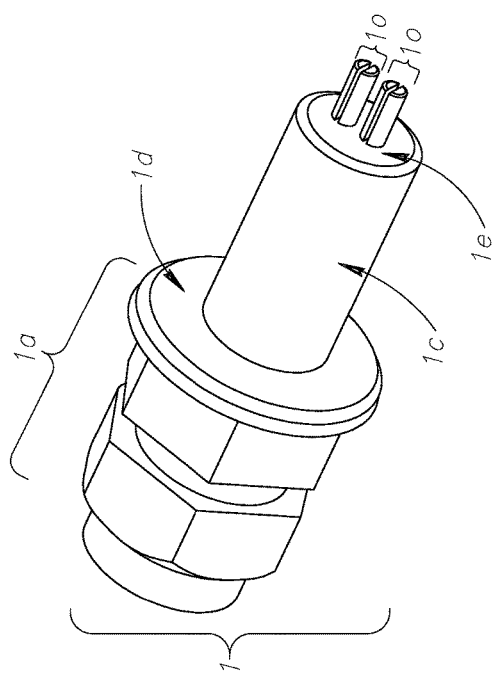
FIG. 1D is a schematic illustration of an angled perspective of a Multi-socket driver tool, according to some embodiments.

As can be seen in FIG. 1E, the Angle Beta ($\beta$) of the distal end of slit 1j of driver pin element and the Angle Alpha ($\alpha$) of the proximal end of slit 1m of driver element may both be varied to generate a specific required tension, for example, where the angle of 1j is preferably greater than the angle of 1m, to create a variable bending tension in pin elements 1o. As can be seen, in general, proximal slit angle $\alpha$ may be smaller than distal slit angle $\beta$, resulting from the construction of split 1f, in accordance with the elastic properties of the materials being used. In general, pins 1o may be constructed from a metal or polymer, for example, a flexible metal or other material, to allow for rigidity balanced with bend-ability, to allow for controlled tension to be generated in accordance with the elasticity properties of the material being used. Of course, pins and/or slits may be constructed with various shapes, forms, materials and positions to generate required forces, in accordance with the requirements of the driver tool 1.

Ac can be seen in FIG. 1A, the prior art (Gottlieb, US Patent application # US2005120838A1) uses a convergent tapering means of his driver pin flexing arms 1b' (polygonal jaws) of the driver element 1o' and the slit 1f between flexing arms 1b' to try to develop wedge tension, however in this invention, inward or negative tapering is used, which works counter-actively thereby preventing engagement. As can be seen in FIGS. 1B-1C, the pin element flexing arms 1b and/or slits if of the present invention may be configured to allow for outward or positive tapering, to allow for a wedge or grip effect to be generated, to support easy gripping of a bolt or screw. As can be seen, Diameter 5 of proximal end (10) of Driver pins element 1o may generally be less than Diameter 6 of distal end of Driver pin elements 1o, in contrast to the prior art. Further, using Imaginary line 8 extending from proximal end 10 of Driver pin element 1o, the Divergent areas 7 of driver pin element 10 distal ends, in the present invention, is what generate spring forces against a socket being engaged, as opposed to Convergent area 9 of driver pin elements 1o' distal ends in the prior art, which provides converging (opposite) tensions of its driver pin elements 1o'.

In accordance with a known engineering principle, a polygonal driver and socket design causes tension on all corners of the polygonal driver when inserted into the socket of the screw/bolt and used to drive said screw/bolt. The cited prior art, with its polygonal driver and socket design (with its single pair of jaws and single slit between said two jaws) adheres to the above cited engineering principle and causes tension on all corners of each of his polygonal jaws of his driver tool when his driver pin elements 1o' are inserted into a polygonal socket of a screw/bolt, resulting in compressive tension and permanent collapse of the slit if between his two jaws in the torque driving direction 1k when attempting to drive the screw/bolt with his driver tool.

Further, as can be seen in FIG. 1D, Head section driver element 1g may include a Head section diver element circumferential groove 1h, to allow for the insertion of a ring securing mechanism, for example, a flexible "o" ring element (not shown), into the groove so that the head can be inserted in a ratchet type wrench (not shown) and secured to the wrench (i.e. so it doesn't fall out of the wrench).

Figure 1F:
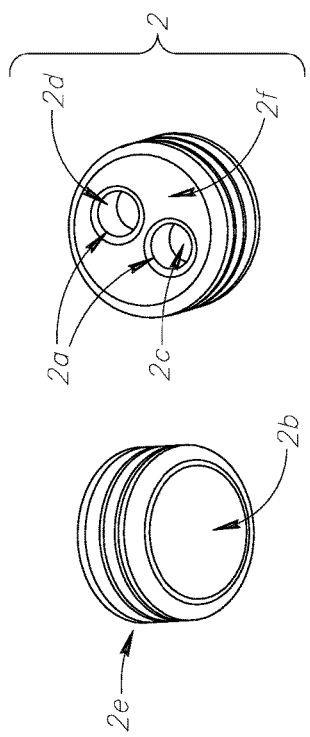
FIG. 1Fa is a schematic illustration of the bottom side of a double socket bolt, according to some embodiments.
Figure 1I:
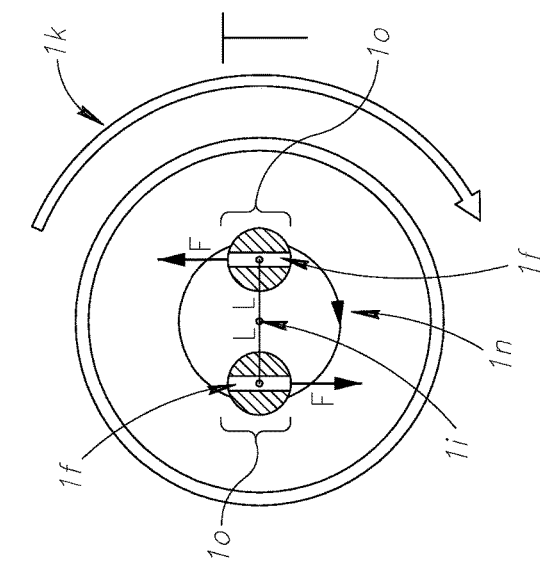
FIGS. 1H-1I are schematic illustrations of a flat perspective of a Socket driver element limiting flange, according to various embodiments.
Figure 1J:
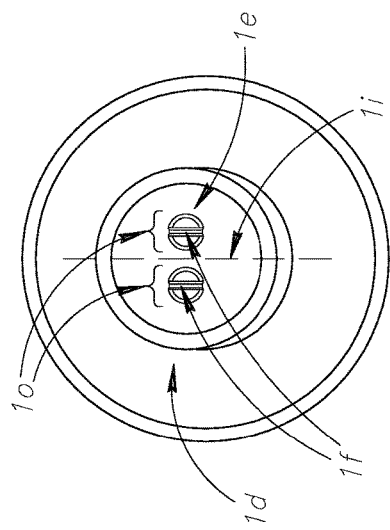
FIG. 1J is a schematic illustration of a raised perspective of a Socket driver element limiting flange, according to some embodiments.
Figure 1H:
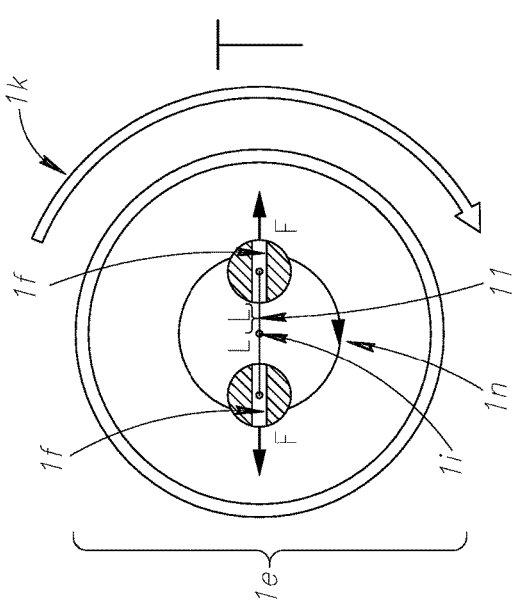

As can be seen in FIG. 1H, the axis of the slits 1f in the respective driver pins of a non-preferred embodiment of the present invention are oriented parallel to an imaginary inner circle 1n around the pins' axes. Such an orientation of the slits if however, would cause inevitable bending and damage to the set of pins 1o when torque force drive direction 1k would be acted on the set of pins 1o by screwing in a screw using the driver tool 1.

As can be seen in FIGS. 1I-1J, the axis of each slit if of each driver pin element 1o of the present invention should preferably be oriented (positioned) at a tangent to the imaginary inner circle 1n around the pins' axes, or perpendicular to the direction of the length of the shaft, which preferably is equivalently perpendicular to the torque direction (movement) of the drive turning 1k of the driver tool 1. Further, slit if axis is further oriented so as to be tangent with the torque force load 1k exerted on the individual pin elements 1o. These orientations of the slit if between each set of flexing arms 1b allows each pair of flexing arms 1b of each driver pin 1o to further resist compression when the driver tool 1 is inserted into the corresponding sockets of the screw/bolt and also when driving the screw/bolt, thereby enhancing the pins' 1o rigidity and strength.

The slits of each driver pin 1o are also further aligned to be relatively or substantially parallel with each other plus or minus up to 5 degrees of offset with each other, depending on the tension requirements. This substantially parallel orientation of each of the slits if to each other allows each set of driver pins 1o to work in unison so that the resulting load compression force generated by the torque on the multiple driver pins (when driving the screw/bolt) will not result in excessive bending of the two flexing arms of each of the driver pins 1o (excessive bending of the pins would compromise their ability to grip subsequent screws/bolts) but rather assures that these same compression forces are in fact more or less equally distributed on each of the flexing arms 1b of each set of driver pins 1o.

It is to be further appreciated that when one takes into consideration that each driver pin 1o is preferably machined so as to be slightly offset in any direction by as little as 50 microns or possibly less in its location relative to the other driver pin 1o this improved design creates a further wedging type grip of the screw/bolt when each driver pin 1o is inserted into each corresponding socket of the screw/bolt.

It is known in engineering that Torque $(T)=2(F*L)$. This equation means that the driving torque load on a driving tool is equal to two times the Force multiplied by the Length (distance) from the center point between the two driver pin sets to the center of each driver pin set (see FIG. 1E). The design of the present invention described above therefore provides an efficient tool for engaging and driving screws/bolts.

As may also be seen in FIGS. 1I-1J, the center point 1i between the two driver pin elements 1o, also defining the Distance from center point to center 1l of each driving pin 1o as L, includes an Angled cut slit if of driver pin 1o, to provide resistance to support the driving force in the direction 1n of the Torque 1k. Of course, other design elements, features or configurations may be used.

It is to be further appreciated that more than two pin elements 1o may be incorporated into the multi-socket driver tool 1 wherein each set of pin elements would individually engage a corresponding number of sockets of the screw/bolt.

With reference to FIGS. 1Fa-1Fb, the driver tools with multiple sockets may find particular benefits when employed with headless bolts/screws 2 and/or with generally short bolts or other connecting elements, may include, for example, screw or Bolt socket 2a with its round internal cross-section, Bottom curved surface 2b, Socket floor 2c, Socket inner side wall 2d, which is preferably unthreaded, Threaded outer side wall 2e, and socket Top surface 2f. Bottom surface 2b, in some embodiments, may function as a stop or limit for the driver tool elements/pins. The bottom surface may be generally flat or may be curved (e.g., concave or convex). Of course, other shapes, design elements, features or configurations may be used.

Based on the above consideration, the frictional engagement of the unique multi-socket driver pin elements of the present invention therefore do not permanently collapse as does the cited prior art when subjected to the repeated stresses both for initial frictional engagement of the improved driver tool into multiple screws/bolts and repeated driving (screwing) of multiple screws/bolts into target sites.

This improved design also allows for the secure frictional engagement by this improved driver tool 1 of very shallow depth multiple sockets in the head of the screw/bolt 2. This is highly useful where the length of the screw/bolt to be used is very short and does not allow for the machining of a standard depth socket into its top surface (i.e. As seen in FIG. 1F, this design can be used to frictionally engage and disengage with screws that are headless as well).

The cross-sectional peripheral outer shape of each pin element of a multi-socket driver must be designed to be able to be inserted into a corresponding cross-sectional socket shape of a screw/bolt. Any shape may be used, however preferably a round shape may be used. In some embodiments, polygonal and curved shapes may be used, as may hexagonal, rectangular, and elliptical shapes. In general, such a multi-socket driver is easier to manufacture compared to a polygonal shaped driver. In addition, such a multi-socket driver generally requires far less accuracy for the user to position the multiple pins in the sockets compared a polygonal shaped driver. Moreover, such a multi-socket driver is preferably designed to withstand higher load forces than polygonal pins, in accordance with a known engineering principle.

According to some embodiments of the present invention, a spring-clip socket driver tool features a built in shaped spring element incorporated into its driving element, where the driving element's main shaft may be round or polygonal in its outer peripheral cross-section, and where the spring element's general shape resembles a clip, though other embodiments may not resemble a clip. The clip-shaped spring element is preferably formed by cutting (for example by wire cutting) a specifically oriented angled open through slit through a specific section of the driver element of the spring-clip driver tool, as is illustrated in the drawings. The angled through slit is preferably designed to extend along a length of the driving element that terminates prior to the end section of the driver element. This design allows for the driving engagement of a solid core end section (without any spring element feature) of the driving element into the socket of the head of the screw/bolt, while separating the frictional engaging element (the spring clip element) from this solid core end driving section of the driving element.

Reference is now made to FIGS. 2A and 2C-2E, which are graphical illustrations of different views of a Spring clip driver tool with associated bolts, according to some embodiments, for enabling multiple use of the driver tool without loss of engagement of the driving element in the socket of fixation/connector elements, and rapid release from the screw or bolt being inserted or extracted, when required. Spring clip driver tool 3 includes Driver shaft body 3a, Spring clip element 3b, Socket driver element tip section 3c, Socket driver engagement element 3d, through slit element 3e, Driver shaft body through slit section 3f, Spring clip longitudinal through slit section 3g, Spring clip vertical through slit section 3h, and Spring clip protruding bulge section 3i. Further, in some embodiments, spring driver tool 3 includes Socket driver element beveled tip 3j, Socket driver bottom surface 3k, Driver shaft body limiting flange 3l, Head section 3m, Socket driver limiting flange 3n, Spring clip outer side wall 3o, and Socket driver tip side wall 3p. Of course, other design elements, features or configurations may be used.

In general, spring clip bulge 3i is preferably formed by cutting away material from the Spring clip outer side wall 3o, and leaving bulge 3i to be smaller than the height of slit 3g, such that 3i will be fully engaged within the diameter of the engaged socket, so as to avoid excessive bending forces when engaged in said socket. Also while 3i is collapsed in an engaged socket, there is substantially minimal tension on the spring clip element 3b, as the clip elements, and specifically the 3i, are substantially below the line of torque force when inserted into the socket of the screw/bolt, and are kept in place using bending force only, to keep an attached bolt or screw engaged, and leaving the outer walls of Socket driver element 3d, including Socket driver tip 3c and its side walls 3p primarily exposed to the torque forces. Of course, slit size and shape and size and shape may be configured so as to optimize the desired spring effects and tensions, in accordance with the elastic properties of metal to be used.

With reference to FIGS. 2F-2G, in additional embodiments, multiple slits may be configured in the shaft body 3a of the Spring clip driver tool 3 extending into the socket driver element 3d so as to machine multiple spring clip elements 3b for the multiple sided engagement of multiple internal walls of the socket of a bolt/screw by the Spring clip driver tool 3. Socket element tip section 3c still maintains a solid core so as to still allow it to function primarily as an initial driving element of this embodiment of the Spring clip driver tool 3. A variable number of spring clip elements may be incorporated into each improved driver depending on the size of the socket and length and weight of the screw/bolt to be used. The spring clip element 3b may include a guiding feature 20, preferably located on a protruding bulge section 3i, such as illustrated in FIG. 2G.

With reference to FIG. 2B, screw or bolt 4 may include Head section 4a, Socket 4b, Threaded shaft 4c, Unthreaded shaft 4d, Socket inner side walls 4e, and Socket floor 4e. Of course, other design elements, features or configurations may be used.

This improved design of the spring-clip socket driver tool allows for the partial separation of the two stress forces (frictional engaging and driving) that are placed on the driving element of the improved driver, wherein the spring clip element (or elements) of the driving element functions to primarily frictionally engage (by direct engagement) the inner side walls of the socket of the head of the screw/bolt and the solid core end of the driving element functions to primarily drive the screw/bolt. This improved design allows for the repeated frictional direct engagement of its unique spring clip driver element, which will not permanently collapse when subjected to the repeated stresses both for initial frictional engagement of the improved driver tool into variable depth polygonal shaped or even round shaped sockets of multiple screws/bolts. This improved driver tool's design also allows for the repeated driving (screwing) of multiple screws/bolts utilizing the spring clip socket driver tool described herein and its easy and rapid release from said socket when the driving of the screw/bolts have been accomplished.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. A driver tool comprising:
   a. a driver shaft having an axis of rotation for driving a screw;
   b. a non-circular driver element protruding from the driver shaft and having a base region proximate the driver shaft and a distal region including a distal end away from the driver shaft, wherein the non-circular driver element includes at least one flexing arm suitable for inserting into a non-circular socket of a screw head of the screw; wherein the flexing arm engages at least one inside wall of the socket using a spring force; and
   wherein the flexing arm extends partially through the driver element, the driver element having a solid tip section at the distal end thereof, thereby providing a slit that does not extend to a top surface of the driver element, whereby the torque force required for driving the non-circular socket screw head is generally decoupled from the frictional force for engaging the non-circular socket of the screw head;
   wherein the slit has a distal opening on a lateral surface of the driver element that is hidden from a top view of the driver tool, wherein the top view is a plan view from directly above the distal end of the non-circular driver element and perpendicular to the axis of rotation.

2. The driver tool of claim 1, wherein the rotational force acting on the non-circular driver element for driving a screw is generally perpendicular to the frictional force for securing the non-circular driver element to the fixation component.

3. The driver tool of claim 1, wherein the driver tool includes a single driver element and any rotational motion of the driver element about the axis of rotation of the driver shaft rotates the screw.

4. The driver tool of claim 1, wherein the flexing arm has a protrusion located near the distal region of the flexing arm and extending away from the center of the non-circular driver element.

5. The driver tool of claim 1, wherein the cross-section of non-circular driver element generally has the shape of a regular hexagon.

6. The driver tool of claim 1, wherein the cross-section of the non-circular driver element is uniform, except for a guide feature and the slit.

7. The driver tool of claim 1, wherein the slit includes a first slit section and a second slit section for defining the flexing arm, wherein the flexing arm is a spring clip, the first slit section is perpendicular to the axis of rotation and extends from a lateral surface of the driver element to the second slit section, and the second slit section is generally longitudinal and tilted relative to the first slit section.

8. The driver tool of claim 1, wherein the driver tool includes a guiding feature that is a taper or curved region on a leading edge of the flexing arm, positioned so that the flexing arm is automatically compressed inward towards the slit when the driver element is inserted into a socket.

9. A process comprising the steps of:
 a. providing a driver tool of claim 1 and a screw having a screw head with a non-circular socket;
 b. engaging the non-circular driver element of the driver tool by inserting the non-circular driver element into the socket of the screw, wherein the flexing arm at least one inside wall of the socket using a spring force;
 c. rotating the driver tool so that the screw is rotated and driven into a component to which it becomes attached; and
 d. disengaging the driver tool from the screw.

10. The process of claim 9, wherein the step of rotating the driver tool creates a driving force on an internal wall of each of the sockets, wherein the driving force is perpendicular to the spring force.

11. The process of claim 9, wherein the flexing arm returns to an initial position upon disengaging the driver tool from the screw.

12. The driver tool of claim 1, wherein the non-circular driver element has an axis in the base to distal direction that is generally parallel to the axis of rotation of the driver shaft; and the driver slit is tilted relative to the axis of rotation.

13. The driver tool of claim 1, wherein
 the rotational force acting on the non-circular driver element for driving a screw is generally perpendicular to the frictional force for securing the driver element to the screw;
 the driver tool includes a single non-circular driver element; has a non-circular shape for inserting into the socket having generally the same non-circular shape so that any rotational motion of the driver element about the axis of rotation of the driver shaft rotates the screw;
 the flexing arm has a protrusion located near the distal region of the flexing arm and extending away from the center of the non-circular driver element;
 a guiding feature is provided, that is a taper or curved region on the leading edge of the flexing arm, positioned so that the flexing arm is automatically compressed inward towards the slit when the driver element is inserted into a socket; and
 the cross-section of the driver element is generally uniform, except for the guide feature and the slit.

14. The driver tool of claim 13, wherein
 the slit includes a first slit section and a second slit section, wherein the first slit section is perpendicular to the axis of rotation and the second slit section is generally longitudinal and tilted relative to the first slit section.

15. The driver tool of claim 1, wherein
 the rotational force acting on the non-circular driver element for driving a screw is generally perpendicular to the frictional force for securing the driver element to the screw;
 the driver tool includes a single non-circular driver element; has a non-circular shape for inserting into the socket having generally the same non-circular shape so that any rotational motion of the driver element about the axis of rotation of the driver shaft rotates the screw;
 the flexing arm has a protrusion located near the distal region of the flexing arm and extending away from the center of the non-circular driver element;
 a guiding feature is provided, that is a taper or curved region on the leading edge of the flexing arm, positioned so that the flexing arm is automatically compressed inward towards the slit when the driver element is inserted into a socket; and
 the cross-section of the driver element is generally uniform, except for the guide feature and the slit.

16. The driver tool of claim 1, wherein the slit is located entirely in the driver element and does not extend into the driver shaft; and wherein the driver element has a uniform cross-section along its length except for the slit and a portion of the flexing arm that extends beyond the uniform cross-section, wherein the uniform cross-section extends to the top of the driver element.

17. The driver tool of claim 1, wherein the driver element has a generally planar top surface that is hexagonal in shape and is free of any slits.

18. The driver tool of claim 1, wherein the distal opening is perpendicular to the axis of rotation; wherein the slit has a distal end and a proximate end and a plane of the slit is tilted relative to the axis of rotation.

19. The driver tool of claim 1, wherein the flexing arm has a wedge-shaped cross-section with a distal end having a first thickness and a proximate end having a second thickness, wherein the second thickness is greater than the first thickness.

20. The driver tool of claim 19, wherein the distal end of the flexing arm is in the distal region of the drive element and the proximate end of the flexing arm is in the driver shaft, wherein the slit is defined by a surface of the flexing arm and a surface of a complementary portion of the drive tool, where the surface of the flexing arm and the surface of the complementary portion of the drive tool are parallel and tilted relative to the axis of rotation, wherein the surface of the flexing arm forms a non-zero acute angle with the axis of rotation, wherein the acute angle is defined by the angle between a plane of the surface and the axis of rotation; and the flexing arm moves radially inwards.

* * * * *